United States Patent [19]

Archibald

[11] 4,322,201
[45] Mar. 30, 1982

[54] IV PUMP WITH BACK PRESSURE CONTROL

[75] Inventor: G. Kent Archibald, White Bear Lake, Minn.

[73] Assignee: AVI, Inc., St. Paul, Minn.

[21] Appl. No.: 77,620

[22] Filed: Sep. 21, 1979

Related U.S. Application Data

[63] Continuation-in-part of Ser. No. 19,233, Mar. 9, 1979, Pat. No. 4,236,880.

[51] Int. Cl.³ .................. F04B 49/08; F04B 39/08
[52] U.S. Cl. .................................. 417/279; 417/507; 128/218 F
[58] Field of Search ............... 128/214 E, 214 F; 417/279, 507, 540, 542

[56] References Cited

U.S. PATENT DOCUMENTS

| | | | |
|---|---|---|---|
| 2,711,134 | 6/1955 | Hughes | 417/479 |
| 3,192,864 | 7/1965 | Notte | 417/542 |
| 3,362,346 | 1/1968 | Bottoms et al. | 417/540 |
| 3,428,042 | 2/1969 | Chesnut | 92/98 RD |
| 3,730,495 | 5/1973 | Elam | 92/98 RD |
| 4,042,153 | 8/1977 | Callahan | 128/214 F |
| 4,121,584 | 10/1978 | Turner | 128/214 E |
| 4,142,524 | 6/1979 | Jassawalla | 128/214 F |
| 4,155,362 | 5/1979 | Jess | 417/477 |
| 4,199,307 | 4/1980 | Jassawalla | 128/214 F |
| 4,210,138 | 8/1980 | Jess | 128/214 F |

Primary Examiner—William L. Freeh
Attorney, Agent, or Firm—Kinney, Lange, Braddock, Westman and Fairbairn

[57] ABSTRACT

A volumetric infusion pump of the type having a rolling diaphragm pumping chamber includes a back pressure sensor between the rolling diaphragm pumping chamber and the pump outlet for sensing back pressure. A valve is positioned between the back pressure sensor and the pump outlet for controlling fluid flow to the pump outlet in order to control back pressure supplied to the rolling diaphragm pumping chamber. Back pressure is maintained within the rolling diaphragm pump chamber so that the rolling diaphragm maintains close contact with the piston even in the event of a negative head pressure at the pump outlet. The valve and the back pressure sensor are preferably linked so that the valve restricts fluid flow to the pump outlet only when the sensed back pressure is less than a predetermined level.

8 Claims, 1 Drawing Figure

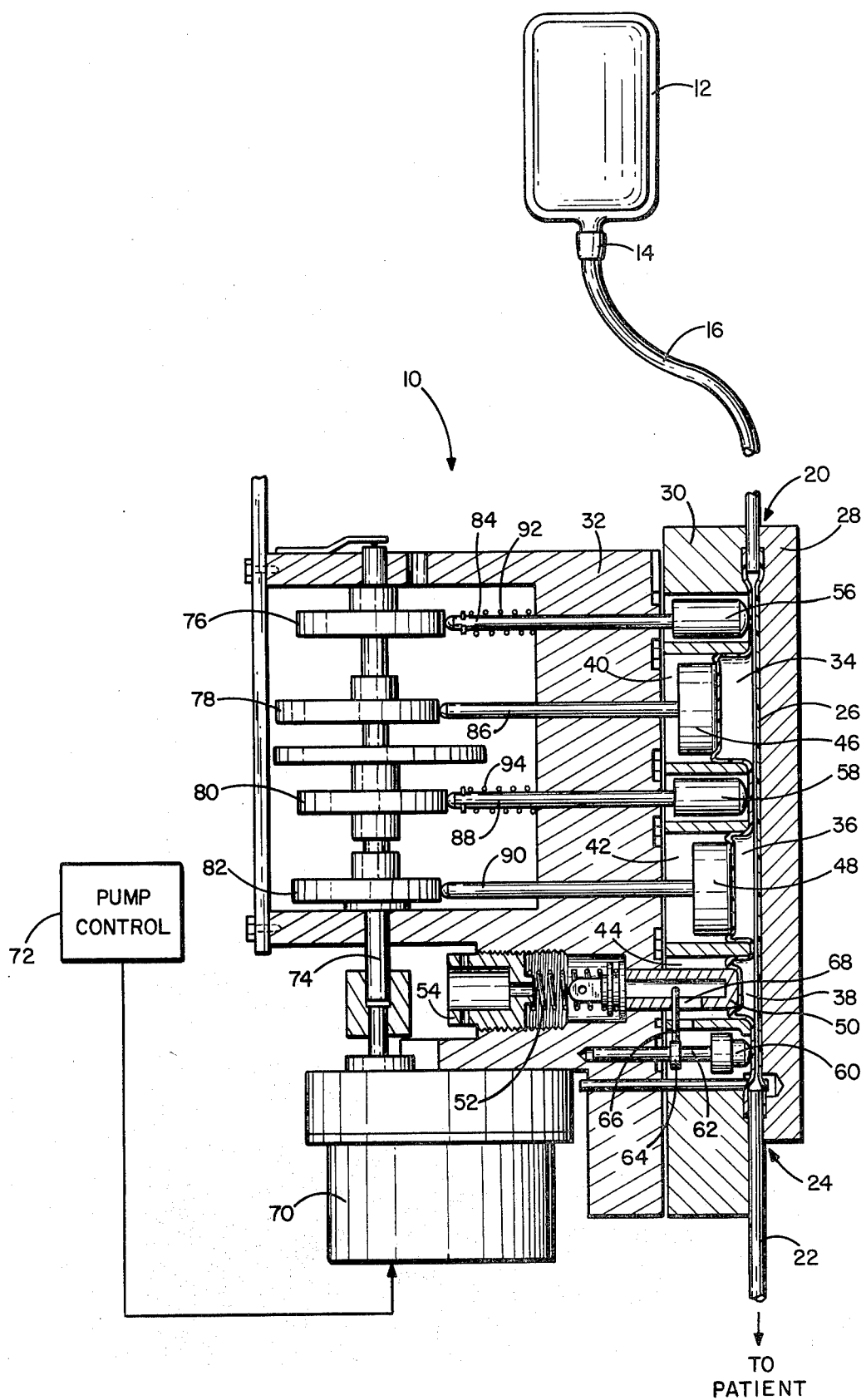

IV PUMP WITH BACK PRESSURE CONTROL

REFERENCE TO CO-PENDING APPLICATION

The present invention is a continuation-in-part of my previously filed U.S. patent application Ser. No. 19,233, filed Mar. 9, 1979, now U.S. Pat. No. 4,236,880 and assigned to the same assignee as the present application.

BACKGROUND OF THE INVENTION

1. Field of the Invention.

The present invention relates to pumping apparatus. In particular, the present invention relates to a rolling diaphragm type pump.

2. Description of the Prior Art.

To improve health care, there has been considerable effort with regard to the administration of intravenous (IV) fluid. For many years IV solutions were administered only by the force of gravity. The volume rate was measured by counting the number of drops per minute. In many instances this method proved unsatisfactory. Drop size is directly proportional to surface tension, which is affected by viscosity, temperature, type of solution, and also drop size is affected by the speed at which the drop forms. The drop rate is affected by the gravitation force and the restrictions of the tube and needle. If a tube is partly occluded, the drop rate will decrease or as the IV supply decreases the hydrostatic pressure will decrease causing a decrease in drop rate. In many cases, therefore, the variability of both the drop size and the drop rate (both of which are for the most part beyond the control of the operator) makes this method of administration of intravenous fluid unsatisfactory.

Improvements have been made by adding an electronic drop counter together with either a controller or a peristaltic pump. The electronic drop counter and controller combination controls the drop rate but makes no improvements in controlling drop size, and also has the deficiency of not being able to control drop rate if back pressure increases beyond the hydrostatic forcing pressure. The electronic drop counter and peristaltic pump combination increase the forcing pressure but lacks an accurate metering method.

Improvement in metering methods results with the use of displacement pumps, which offer the capability of greater precision in controlling IV flow rates than is possible with the prior art IV controllers which depend on gravity. These pumps, in addition to metering the fluid, also apply positive pressure to the fluid or the IV tubing.

SUMMARY OF THE INVENTION

The volumetric infusion pump of the present invention has a pump inlet, a pump outlet, and a rolling diaphragm pumping chamber means connected between the pump inlet and the pump outlet. The rolling diaphragm pumping chamber means includes at least a first cylinder, a first piston, and first flexible diaphragm means defining a pumping chamber. Movement of the piston with respect to the cylinder varies the volume of the chamber defined by the flexible diaphragm means.

During the pumping cycle, it is required that the flexible diaphragm means maintain close contact with the piston as the piston moves. If there is a negative head pressure at the outlet of the pump, the flexible diaphragm means may lose contact with the piston, thereby causing a volume error.

In the present invention, a positive pressure is maintained in the pumping chamber in order to maintain contact between the flexible diaphragm means and the piston. This is achieved by valve means positioned between the rolling diaphragm pumping chamber means and the pump outlet for controlling fluid flow to the outlet and thereby controlling the back pressure supplied to the pumping chamber means.

In a preferred embodiment of the present invention, the pump also includes back pressure sensing means connected between the rolling diaphragm pumping chamber means and the valve means for sensing back pressure. The back pressure sensing means and the valve means are preferably connected so that the valve means controls the fluid flow to the pump outlet as a function of back pressure sensed by the back pressure sensing means.

BRIEF DESCRIPTION OF THE DRAWINGS

The FIGURE shows a sectional view of an intravenous pump including the back pressure control valve means of the present invention.

DETAILED DESCRIPTION OF THE PREFERRED EMBODIMENTS

The FIGURE illustrates the present inventon, which includes an IV pump 10 of the general type described in my co-pending application Ser. No. 19,223. A detailed description of pump 10 is contained in that co-pending application, and a detailed description of the entire pump and its operation will not be repeated.

In the FIGURE, a supply bag or reservoir 12 containing IV fluid is connected to drop chamber 14, which in turn is connected by tubing 16 to inlet 20 of pump 10. Outlet tubing 22 is connected to outlet 24 of pump 10, and terminates at a needle (not shown) which is inserted into the patient.

Pump 10 includes disposable pump chamber 26, which is connected at its inlet and outlet ends to tubing 16 and 22, respectively. Disposable pump chamber 26 is inserted within a pump housing which includes top cover 28, diaphragm enclosure 30, and cam housing 32.

Disposable pump chamber 26 contains three flexible rolling diaphragm chambers 34, 36 and 38. Chambers 34 and 36 are first and second pumping chambers, respectively, while chamber 38 is a pressure monitoring chamber which moves in response to back pressure on fluid passing from chamber 26 through outlet tubing 22.

Diaphragm enclosure 30 includes first, second and third cylinders 40, 42 and 44 which receive rolling diaphragm chambers 34, 36 and 38, respectively. First piston 46 is movable within first cylinder 40 to vary the volume of first pumping chamber 34. Similarly second piston 48 is movable within second cylinder 42 to vary the volume of second pumping chamber 36. Both first piston 46 and second piston 48 are motor driven, as will be discussed later.

Unlike first and second pistons 46 and 48, third piston 50 is not motor driven, but rather is movable within third cylinder 44 in response to the fluid pressure in sensing chamber 38. Spring 52 urges third piston 50 in a direction which opposes the force of the fluid back pressure within chamber 38. The spring force applied by spring 52 is adjustable by threaded spring holder 54. The operation of the back pressure sensor formed by third chamber 38, third cylinder 44 and third piston 50 is described in detail in my previously mentioned copending application.

First and second valves 56 and 58 are also provided within diaphragm enclosure 30. First valve 56 is positioned between inlet 20 and first pumping chamber 34. First valve 56 is motor driven, and when in its uppermost position, pinches off the flexible portion of disposable pumping chamber 10 between inlet 20 and first pumping chamber 34. When in its lowermost position first valve 56 permits fluid flow from inlet tubing 16 to first pumping chamber 34.

Similarly, second valve 58 is positioned between first and second pumping chambers 34 and 36. Second valve 58 is also motor driven, and when in its uppermost position, pinches off the flexible portion of disposable pumping chamber 26 between first pumping chamber 34 and second pumping chamber 36. When in its lowermost position, second valve 58 permits fluid flow from the first pumping chamber 34 to the second pumping chamber 36.

Also shown in the FIGURE is third valve 60 which is attached to shaft 62 and is linked through collar 64 and arm 66 to slot 68 in third piston 50. When pressure in third chamber 38 reaches a low level, the lower end of slot 68 engages arm 66 and forces third valve 60 against the flexible portion of disposable chamber 26 between third chamber 38 and outlet 24. Valve 60, therefore, causes a slight positive back pressure within chambers 34, 36 and 38 which prevents the chambers from collapsing. At higher back pressures, third piston 50 moves downward so that arm 66 no longer engages the bottom of slot 68 and third valve 60 is no longer forced against the portion of disposable chamber 26 between third chamber 38 and outlet 24. In my previously mentioned co-pending application the back pressure providing function is performed by a leaf spring which applies a slight force to the top half of the disposable chamber.

Supported on cam housing 32 is motor 70, which is preferably a stepper motor. Motor 70 is controlled by pump control 72, which preferably includes a microcomputer control circuit (not shown). Pump control 72 controls the speed of motor 70, and when an alarm condition is sensed, pump control 72 causes motor 70 to stop, thereby terminating the operation of the pump.

Motor 70 drives cam shaft 74 with attached cams 76, 78, 80 and 82. Cam 76 drives first valve 56 through cam follower rod 84, which has its lower end rounded to ride on cam 76 and which is attached at its upper end to first valve 56.

Cam 78 drives first piston 46 through cam follower rod 86. The lower end of rod 86 rides on cam 78, while the upper end is threaded to permit attachment to first piston 46.

Second valve 58 is driven by cam 80 through cam follower rod 88, which is rounded at its lower end to ride on cam 80. The upper end of rod 88 is attached to second valve 58.

Cam 82 drives second piston 48 by means of cam follower rod 90. The lower end of rod 90 is rounded to ride upon the surface of cam 82, and the upper end of rod 90 is threaded for connection to second piston 48.

Cam follower rods 84 and 88 have small springs 92 and 94 to urge the ends of rods 84 and 88 against their respective cams 76 and 80.

During normal operation, first piston 46 and first valve 56 are initially at their uppermost position, and second piston 48 and second valve 58 are in their lowermost position. Second valve 58 then closes, and shortly thereafter first valve 56 moves downward to open. At this point, fluid from bag 12 is supplied through inlet tubing 16 and begins to fill first chamber 34. This drives piston 46 downward and maintains follower rod 84 in contact with cam 78. The downward movement of piston 80 draws additional fluid from supply bag 12, past open first valve 56 and into chamber 34 at a rate which is limited by the cam 78 surface.

At the same time first chamber 34 is filling, second piston 48 is moving on an upstroke, thereby reducing the volume of second chamber 36 and pumping fluid from second chamber 36 through outlet tubing 22 to the patient.

When the first piston 46 reaches its lowermost position and second piston 48 is approaching its uppermost position, first valve 56 is driven upward to close fluid flow from supply bag 12 to first chamber 34. Second valve 58 is then moved downward to permit fluid flow from first chamber 34 to second chamber 36. After the two valves have been moved, piston 46 begins to move upward, thereby reducing the volume of first chamber 34, while second piston 48 moves downward, thereby increasing the volume of second chamber 36. The rate of decrease of the volume of first chamber 34 is preferably greater than the rate of increase of second chamber 36. As a result, some of the fluid being pumped from first chamber 34 is pumped out through outlet tubing 32 to the patient. By proper selection of the cross-sectional areas of chambers 34 and 36 and the rate of travel of pistons 46 and 48, the amount of fluid being pumped out through outlet tubing 22 may be essentially the same throughout the entire pumping cycle.

The back pressure control of the present invention, which is provided by means of the back pressure sensor and third valve 60 is necessary because disposable pump chamber 26 is a replaceable and disposable unit. As a result, the portions of the disposable pump chamber 26 forming flexible rolling diaphragm chambers 34, 36 and 38 cannot be attached to either first, second and third cylinders 40, 42 and 44, or to first, second and third pistons 46, 48 and 50.

In order to avoid volume pumping errors during the pumping cycle, it is required that as first piston 46 moves on an upstroke, that first rolling diaphragm chamber 34 maintain close contact with first piston 46. If, however, there is a negative head pressure at outlet 24, diaphragm 34 could lose contact with piston 46 and in effect collapse since it is not attached to piston 46. This would cause a volume pumping error.

The purpose of the present invention is to maintain a positive pressure in the pumping chamber so as to maintain the diaphragm in contact with the pistons at all times, even in the event of a negative pressure at outlet 24. This is achieved by third valve 60 in conjunction with third piston 50.

As shown in the FIGURE, third valve 60 is linked by collar 64 and arm 66 to slot 68 in third piston 50. When pressure in third chamber 38 reaches a low level, the lower end of slot 68 engages arm 66 and forces third valve 60 against a flexible portion of disposable chamber 26. This causes a partial occlusion of the passage to outlet 24. Spring 52 forces third piston 30 upwards and, through the linkage of arm 66 and collar 64, forces third valve 60 upward to close or partially occlude the passage to outlet 24.

The back pressure created when valve 60 is forced upward is based upon the spring force of spring 52. This force can be adjusted by turning threaded spring holder 54 to either increase or decrease the compression of spring 52.

In the embodiment shown in the FIGURE, the effective area of third valve 60 in creating a slight positive pressure in the pumping chamber is increased by the amount of cross-sectional area of piston 50. This results in less pump pressure being required to open third valve 60. As a result, a larger force can be used to bias third valve 60 than is possible if valve 60 and third piston 50 are not linked together.

Under normal conditions in which a positive pressure exists at outlet 24, the back pressure within the pressure sensing chamber 38 forces third piston downward in opposition to the force of spring 52. Arm 66 no longer engages the bottom of slot 68, and therefore the force applied to third valve 60 is removed. The back pressure supplied by means of valve 60, therefore, is not additive to the pump output pressure at outlet 24. If the spring force supplied by spring 50 is adjusted so that the 0 psi at outlet 24 the pumping chambers have a back pressure of 2 psi, then at 10 psi at outlet 24 the pump chamber is only 10 psi (not 12 psi). This is because valve 60 is effectively disconnected from spring 52 as soon as a sufficient back pressure is present within pressure sensing chamber 38 to force arm 66 out of engagement with the bottom of slot 68.

In conclusion, the present invention permits the use of a disposable rolling diaphram type pumping chamber even in the event of a condition in which negative head pressure is present at the outlet. This reduces pumping errors. In addition, the back pressure provided by the preferred embodiment of the invention shown in the FIGURE is not additive to the pump output pressure, so that pump efficiency is not significantly degraded.

Although the present invention may utilize the back pressure sensor and third valve which operate independently, the embodiment shown in the FIGURE is particularly advantageous. By coupling together the back pressure sensor and third valve 50, an increased spring force can be used in biasing valve 60. Tolerances in the compliance of the flexible material forming disposable pumping chamber 26 are less critical, since third valve 60 only applies pressure against the flexible material when a low pressure condition is sensed by the pressure sensor.

Although the present invention has been described with reference to preferred embodiments, workers skilled in the art will recognize that changes may be made in form and detail without departing from the spirit and scope of the invention.

What is claimed is:

1. A volumetric infusion pump for pumping fluid from a reservoir to a patient, the volumetric infusion pump comprising:
   a pump inlet for connection to the reservoir;
   a pump outlet for connection to the patient;
   rolling diaphragm pumping chamber means connected between the pump inlet and the pump outlet;
   pressure sensing means connected between the rolling diaphragm pumping chamber means and the pump outlet for sensing pressure; wherein the pressure sensing means comprises:
   a cylinder;
   a piston movable in the cylinder;
   flexible diaphragm means between the cylinder and the piston defining a pressure sensing chamber; and
   spring bias means for applying a force urging the piston in a direction which reduces the volume of the pressure sensing chamber, and wherein pressure in the pressure sensing chamber applies a force urging the piston in a direction which increases the volume of the pressure sensing chamber; and
   valve means between the pressure sensing means and the pump outlet for controlling fluid pressure in the rolling diaphragm pumping chamber means wherein the valve means restricts a flow passage between the pumping chamber means and the pump outlet to increase pressure in the rolling diaphragm pumping chamber means if the pressure sensed by the pressure sensing means is less than a predetermined level, and wherein the valve means does not restrict the flow passage if the pressure sensed is greater than the predetermined level.

2. The volumetric infusion pump of claim 1 and further comprising:
   linkage means for linking the valve means and the piston when the pressure is less than the predetermined level.

3. The volumetric infusion pump of claim 2 wherein the linkage means comprises:
   a longitduinal slot in the piston; and
   arm means fixedly connected to the valve means and having a free end extending into the slot, wherein the arm engages one end of the slot and imparts force from the spring bias means to the valve means when pressure in the pressure sensing chamber is less than the predetermined level, and where a pressure in the pressure sensing chamber of greater than the predetermined level causes the piston to move to a position in which the end of the arm means is not engaging an end of the slot, thereby disconnecting the spring bias means and the valve means.

4. A volumetric infusion pump for pumping fluid from a reservoir to a patient, the volumetric infusion pump comprising:
   a pump inlet for connection to the reservoir;
   a pump outlet for connection to the patient;
   pumping chamber means connected between the pump inlet and the pump outlet; and
   pressure sensing and regulating means connected between the pumping chamber means and the pump outlet for sensing a pressure indicative of fluid pressure in the pumping chamber means and controlling the fluid pressure in the pumping chamber means as a function of the sensed pressure to maintain the fluid pressure in the pumping chamber means at least at a predetermined level even if pressure at the pump outlet is less than the predetermined level; wherein the pressure sensing and regulating means allows the fluid pressure in the pumping chamber means to equal the pressure at the pump outlet if the pressure at the pump outlet exceeds the predetermined level; and wherein the pressure sensing and regulating means comprises:
   a cylinder;
   a piston movable in the cylinder;
   flexible diaphragm means between the cylinder and the piston defining a pressure sensing chamber;

valve means for occluding an outlet of the pressure sensing chamber as a function of the position of the piston.

5. The volumetric infusion pump of claim 4 wherein the pumping chamber means includes at least one rolling diaphragm pumping chamber.

6. The volumetric infusion pump of claim 4 and further comprising:
linkage means for linking the valve means and the piston when the sensed pressure is less than the predetermined level.

7. The volumetric infusion pump of claim 6 wherein the linkage means comprises:
a longitudinal slot in the piston; and
arm means fixedly connected to the valve means and having a free end extending into the slot, wherein the arm engages one end of the slot and imparts force from the spring bias means to the valve means when pressure in the pressure sensing chamber is less than the predetermined level, and wherein a pressure in the pressure sensing chamber of greater than the predetermined level causes the piston to move to a position in which the end of the arm means is not engaging an end of the slot, thereby disconnecting the spring bias means and the valve means.

8. A volumetric infusion pump for pumping fluid from a reservoir to a patient, the volumetric infusion pump comprising:
a pump inlet for connection to the reservoir;
a pump outlet for connection to the patient;
pumping chamber means connected in a fluid flow path between the pump inlet and the pump outlet;
a pressure sensing chamber connected in the fluid flow path between the pumping chamber means and the pump outlet for receiving fluid from the pumping chamber means and including a cylinder and a piston movable in the cylinder as a function of fluid pressure of the fluid contained in the pressure sensing chamber, the fluid pressure of the fluid in the pressure sensing chamber being a function of the fluid pressure in the pumping chamber means;
spring bias means for applying a force urging the piston in a direction which reduces the volume of the pressure sensing chamber, and wherein fluid pressure of the fluid contained in the pressure sensing chamber applies a force urging the piston in a direction which increases the volume of the pressure sensing chamber; and
valve means positioned along the fluid flow path between the pressure sensing chamber and the pump outlet for occluding an outlet of the pressure sensing chamber as a function of the position of the piston to maintain the fluid pressure in the pumping chamber at least at a predetermined level even if pressure at the pump outlet is less than the predetermined level; and wherein the valve means allows the fluid pressure in the pumping chamber means to equal the pressure at the pump outlet if the pressure at the pump outlet exceeds the predetermined level.

* * * * *